(12) United States Patent
Scheinberg et al.

(10) Patent No.: US 8,486,409 B2
(45) Date of Patent: *Jul. 16, 2013

(54) ALPHA-EMITTING CONSTRUCTS AND USES THEREOF

(75) Inventors: David A. Scheinberg, New York, NY (US); Michael R. McDevitt, Bronx, NY (US); Dangshe Ma, Millwood, NY (US); George Sgouros, Ellicott City, MD (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/799,186

(22) Filed: Apr. 20, 2010

(65) Prior Publication Data

US 2010/0278727 A1  Nov. 4, 2010

Related U.S. Application Data

(60) Division of application No. 09/721,864, filed on Nov. 24, 2000, now Pat. No. 7,736,651, which is a continuation-in-part of application No. PCT/US99/11673, filed on May 26, 1999, now abandoned.

(60) Provisional application No. 60/086,772, filed on May 26, 1998.

(51) Int. Cl.
*A61K 39/395* (2006.01)
*A61K 51/10* (2006.01)

(52) U.S. Cl.
CPC .................................. *A61K 51/1045* (2013.01)
USPC ....... 424/182.1; 424/1.1; 424/1.49; 424/1.69; 424/9.1; 424/9.3; 424/9.34; 424/130.1; 424/138.1; 424/143.1; 424/152.1; 424/155.1; 424/156.1; 424/174.1; 424/178.1; 424/600; 424/653; 534/10; 534/11; 252/625; 530/391.3; 530/391.7

(58) Field of Classification Search
USPC ................. 424/1.1, 1.49, 1.69, 9.1, 9.3, 9.34, 424/130.1, 138.1, 143.1, 152.1, 155.1, 156.1, 424/174.1, 178.1, 182.1, 600, 653; 534/10, 534/11; 252/625; 530/391.3, 391.7

See application file for complete search history.

(56) References Cited

U.S. PATENT DOCUMENTS 6,683,162 B2 * 1/2004 Scheinberg et al. ............ 534/11

OTHER PUBLICATIONS

Zalutsky, M.R., et al. Cancer Research 54: 4719-4725, 1994.*
Siddiqui, B., et al. Cancer Research 44: 5262-5265, 1984.*
Knox, S. J., et al. Clinical Cancer Research, 2: 457-470, 1996.*
Kennel, S.J., et al, Nuclear Medicine & Biology, 25: 241-246, Apr. 1998.*
Kotz, D., The Journal of Nuclear Medicine, 39(2): 17N-19N, 36N, Feb. 1998.*
Jurcic, J.G., Cancer Research (Suppl. 55):5908-5910, 1995.*
Jurcic, J.G, et al. Cancer Chemotherapy and bilogical Response Modifiers Annual 17, Chapter 10, pp. 195-216, 1997.*

* cited by examiner

*Primary Examiner* — Misook Yu
*Assistant Examiner* — Anne Holleran
(74) *Attorney, Agent, or Firm* — Benjamin Aaron Adler

(57) ABSTRACT

The present invention discloses alpha particle emitting, radioactive constructs capable of killing large tumors (>1 mm in diameter), or other cells involved in human or animal diseases such as virus infected cells, autoimmune cells, or other pathological cells, including normal cells, that are targets for destruction, to achieve a therapeutic result. The alpha-emitting constructs have high specific activity.

12 Claims, 9 Drawing Sheets

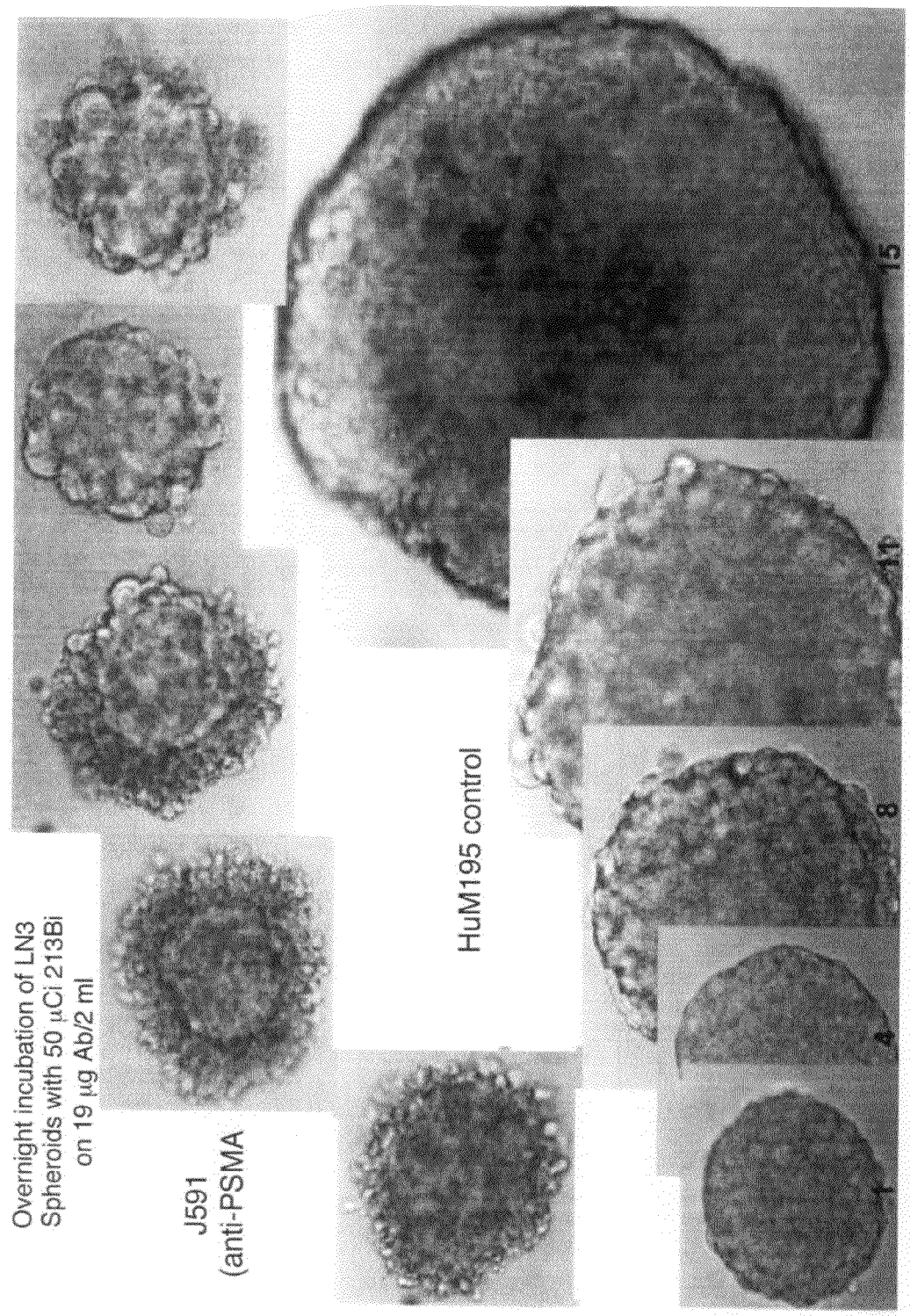

ALPHA-EMITTING CONSTRUCTS AND USES THEREOF

CROSS-REFERENCE TO RELATED APPLICATION

This application is a divisional under 35 U.S.C. §120 of application U.S. Ser. No. 09/721,864, filed Nov. 24, 2000, now U.S. Pat. No. 7,736,651, which is a continuation-in-part under 35 U.S.C. §120 of international application PCT/US1999/11673, filed May 26, 1999, now abandoned, which claims benefit of priority under 35 U.S.C. §119(e) of provisional application U.S. Ser. No. 60/086,772, filed May 26, 1998, now abandoned.

BACKGROUND OF THE INVENTION

1. Field of the Invention

The present invention relates generally to the field of radioimmunotherapy. More specifically, the present invention relates to alpha-emitting constructs with high specific activity and their uses to kill large tumors or other cells involved in human disease states.

2. Description of the Related Art

In radiolabeled antibody therapy, an antibody/radionuclide combination that has been optimized for bulky disease is not optimal for targeting minimal disease (1). Radionuclides that emit long-range beta particles, for example, are generally considered appropriate for targeting bulky disease because their range compensates for the non-uniform antibody distribution that is typical of gross disease. These radionuclides, however, are inappropriate for targeting single cells (2-3).

Antibody forms such as fragments that penetrate solid tumor more rapidly do so at the expense of affinity. In targeting smaller, more penetrable clusters, such agents are only left with the disadvantage of reduced affinity. This is in contrast to chemotherapy wherein a greater effectiveness against bulky disease is also applicable to minimal disease. Radiolabeled antibody therapy is fundamentally different from chemotherapy in its mechanism of action. Although well-justified for chemotherapy, the "solid-tumor hurdle" is not appropriate for radioimmunotherapy (4).

To target bulky disease, intravenously administered antibody must extravasate, diffuse across an interstitial fluid space and then distribute throughout antigen positive cells (FIG. 1A). Each of these steps is associated with a barrier to delivery (5-11). By targeting hematologically distributed single tumor cells or tumor cell clusters, the barriers to antibody delivery are diminished (FIG. 1B). The apparent therapeutic dependence on cluster size and tumor burden is consistent with modeling analyses and experimental observations of antibody penetration (12).

In targeting disseminated tumor cells or micrometastases, each tumor cell must express the antigen. This seemingly severe requirement may be countered by taking advantage of the unique aspects of micrometastatic targeting. Intravenously administered antibody will not be rapidly accessible to potentially cross-reactive cells on the epithelial side of the vasculature. It is possible, therefore, to relax the requirements of antibody specificity when targeting rapidly accessible, hematologically distributed disease by using shorter-lived radionuclides which will have decayed before antibody extravasation. By relaxing the requirement for specificity, antigens that have a higher and more uniform expression on tumor cells may be selected (13).

Bismuth-213 or 212 conjugated alpha-emitting IgG ligands have been proposed to be useful in humans in killing single cells only. These ligands have not thought to be useful in killing solid tumors or small micrometastatic collections of cells only. These single cells or clusters of cells are found in the blood, bone marrow, lymph nodes, liver, and spleen or in regional collections as small metastatic deposits such as in the cerebrospinal fluid, ascites or pleural fluids of patients with leukemia and other cancers ("For Bi-213, no specific killing was observed, which is an indication for the limited applicability of this radionuclide in the treatment of solid tumors."; 14-20). This universally held belief of the application of alpha particle emitters to single cells was based on the short path length of the alpha particles (<100 micrometers), equal to about 2-4 cell diameters and the short half-life of the nuclides (<1 hr). Because the alpha particle emitter decays largely within 3-4 hours, and the time for an IgG to diffuse into a large tumor is on the order of days, there was thought to be little possibility that an IgG carrying Bi-213 or Bi-212 could penetrate beyond 1 or 2 cells to achieve cell kill. Hence, only single cells in the blood, marrow, liver or spleen would be reasonable targets. It is for that reason that the initial studies have focused on leukemias, peritoneal metastases, cancerous meningitis in the cerebrospinal fluid, or micromestastic deposits in the bone marrow.

Strategies to use small quantities, 5-20 mCi, of Bi-213 on labeled ligands have been proposed to kill individual cells such as cancer cells. This strategy involves the use of single doses of Bi-213 labeled antibody or other ligands. However, these methods alone do not enable the use of alpha particle emitting constructs because they fail to take into account the necessity for high specific activity ligands in order for specific cell kill to occur. This necessity arises from the particular nature of the alpha particle emission, i.e., high linear energy transfer and extremely short range, which does not exist for the beta or gamma emissions that have previously been used therapeutically in humans. As a consequence, whereas a beta emitting therapeutic antibody which kills in a field of radiation may be effective at any number of specific activities, an alpha-emitting antibody will only be effective if a minimum of one atom can be delivered to each cell, resulting in at least 1 alpha track through the cell.

The prior art is deficient, first, in understanding the importance of and requirement for the high specific activity in the process of cell kill with an alpha particle, and second, in understanding how one might kill tumors with more than a small number of cells. Therefore, the prior art is deficient in the lack of effective means of killing large tumors (>1 mm in diameter) or other cells involved in human or animal diseases using the high specific alpha-emitting constructs. The present invention fulfills this long-standing need and desire in the art.

SUMMARY OF THE INVENTION

The present invention discloses Bismuth-213 labeled, alpha particle emitting, radioactive constructs capable of killing large tumors, >1 mm in diameter, or other cells involved in human or animal diseases such as virus infected cells, autoimmune cells, or other pathological cells, including normal cells, that are targets for destruction, to achieve a therapeutic result. Methods to kill large tumors, previously thought to be impossible due to the short range of the alpha particles, are described and documented in vitro and in vivo against a human cancer model. The necessity for high specific activity constructs (the number of isotope atoms per ligand molecule) to enable therapeutic results is shown. The necessity for even higher specific activity to achieve "cure" of a cancer, also known as "tumor control probability (TCP)" of one, is also described. These concepts have not been disclosed before in the art, or have been taught away from in the art, and hence, are unexpected.

The present invention also investigates possible therapeutic activities of a longer-lived alpha-emitting nuclide (Ac-225) with multiple alpha-emitting daughters. New chelates containing Ac-225 and its daughters are examined.

Drugs based on alpha-emitting particles can be prepared and administered safely and repeatedly without extramedullary toxicity. The drug made from Bi-213 labeled constructs displayed pharmacokinetics consistent with rapid, specific, and stable targeting only to appropriate cancer cell sites. Significant anti-leukemic activity was seen at the lowest level. Drugs made from Ac-225 labeled constructs are shown to be more potent, as much as 1000 fold more on a mCi basis, than Bi-213 constructs.

In one embodiment of the present invention, there is provided a method of killing a large tumor comprising the step of administering an alpha-emitting construct to the tumor repeatedly. Specifically, the tumor is larger than 1 mm in diameter. Representative examples of alpha-emitting constructs include an antibody, a fragment, a cytokine, a receptor ligand and a ligand of any other kind. Preferably, the alpha-emitting construct is labeled by bismuth-213, bismuth-212, actinium-225, radium-223, lead-212, terbium-149, fermium-155 or astatine-211. The construct should have a high specific activity of from about 0.05 mCi/mg to about 100 mCi/mg. Further, the alpha-emitting construct is administered by repeated dosing in a range of from about 0.1 mg/m$^2$ to about 10 mg/m$^2$.

In another embodiment of the present invention, there is provided a method of killing a non-malignant cell in a human comprising the step of administering an alpha-emitting construct to the cell. Representative examples of alpha-emitting constructs include an antibody, a fragment, a cytokine, a receptor ligand and a ligand of any other kind. Preferably, the alpha-emitting construct is labeled by Bismuth-213, Bismuth-212, actinium-225, radium-223, lead-212, terbium-149, fermium-155 or astatine-211. More preferably, the construct has a high specific activity of from about 0.05 mCi/mg to about 100 mCi/mg, depending on the particular isotope, and is administered in an effective dosage of from about 0.1 mg/m$^2$ to about 50 mg/m$^2$. Preferably, the non-malignant cell is selected from the group consisting of a virus-infected cell, an autoimmune cell, a lymphoid cell, a normal bone marrow cell and an overgrown normal cell. Representative examples of diseases that may be treated using this method include non-neoplastic disease, viral infection, autoimmune disease, prostatic hypertrophy, coronary disease and other vascular occlusive disease.

In another embodiment of the present invention, there is provided a method of killing a tumor by targeting antigens in the tumor vasculature of an individual in need of such of such treatment, comprising the step of: administering to said individual a pharmacologically effective dose of a construct comprising an alpha-emitting isotope effective to inhibit the function of said tumor vasculature.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows solid-tumor targeting. Antibody (Y) must first extravasate from the capillary (cylinder), then diffuse across an interstitial fluid pressure gradient (arrows) to reach the tumor cells (spheres). FIG. 1B shows targeting hematologically distributed micrometastases. Antibody extravasation and diffusion across the interstitial fluid are not necessary. Single tumor cells are directly accessible.

FIG. 2 shows killing of large spheroids as one would "peal an onion." Both spheroid sequences show images obtained after an overnight incubation with Bi-213-labeled antibody. The top sequence shows that treatment with the PSMA specific antibody kills a layer of cells around a core that does not grow further. Additional rounds of treatment will then eliminate the core. In contrast, the spheroids in the lower sequence were treated with a control nonspecific construct and continue to grow.

FIG. 3A shows cytotoxicity with (Bi-212)CHX-A-DTPA-HuM195 as a function of specific activity and dose: 0.2 mCi/mg (HL60: dotted lines, open symbols and RAJI: solid lines, closed symbols) 0.2 mCi/mg (crosses), 10 mCi/mg (circles), 20 mCi/mg (diamonds) and 30 mCi/mg (squares). FIG. 3B shows cytotoxicity of (Bi-213)CHX-A-DTPA-HuM195 as a function of specific activity and dose. RAJI: (closed symbols) 2 mCi/mg (circles) and 8 mCi/mg (triangles); HL60: (open symbols) 1 mCi/mg (triangles), 2 mCi/mg (circles), 4 mCi/mg (diamonds) and 8 mCi/mg (squares).

DETAILED DESCRIPTION OF THE INVENTION

Figure 1A:
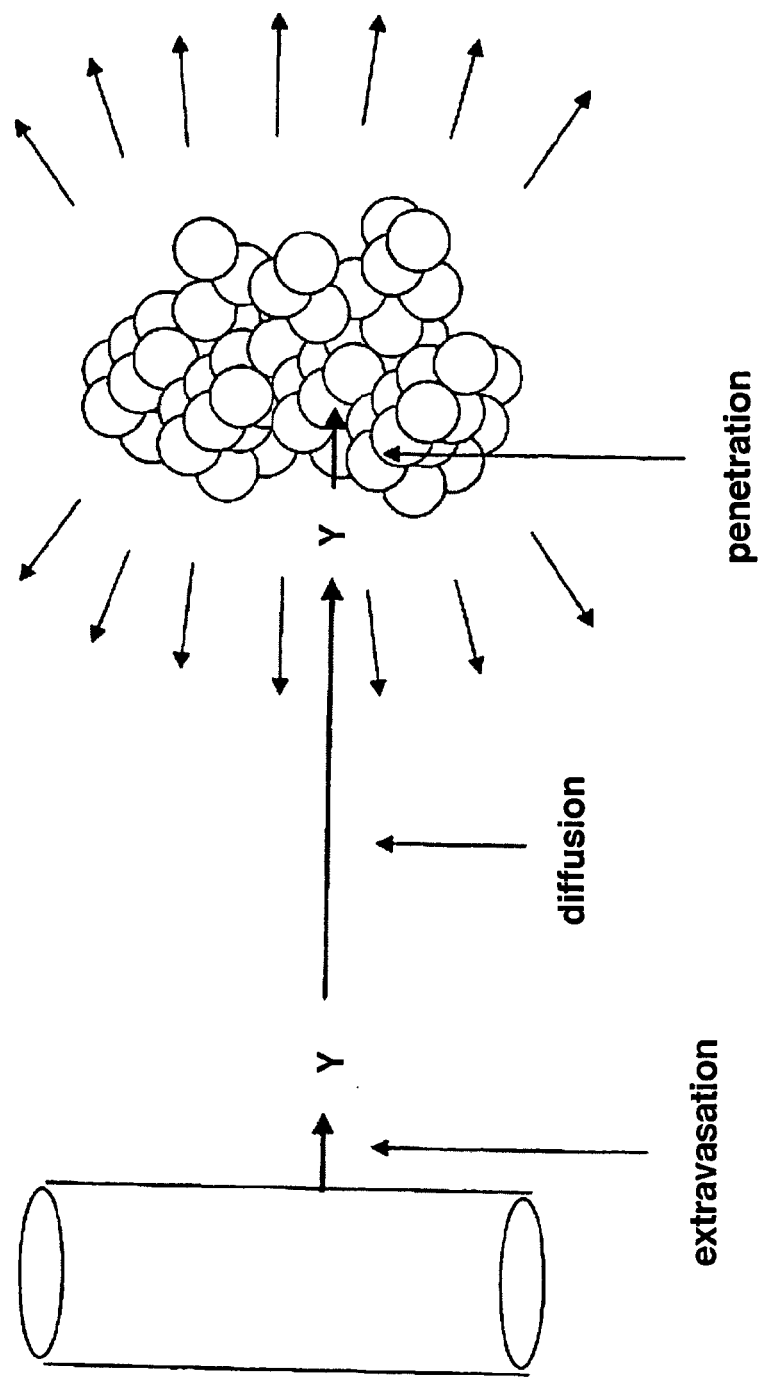
FIGS. 1A-1B show barriers to antibody targeting of tumor cells.
Figure 1B:
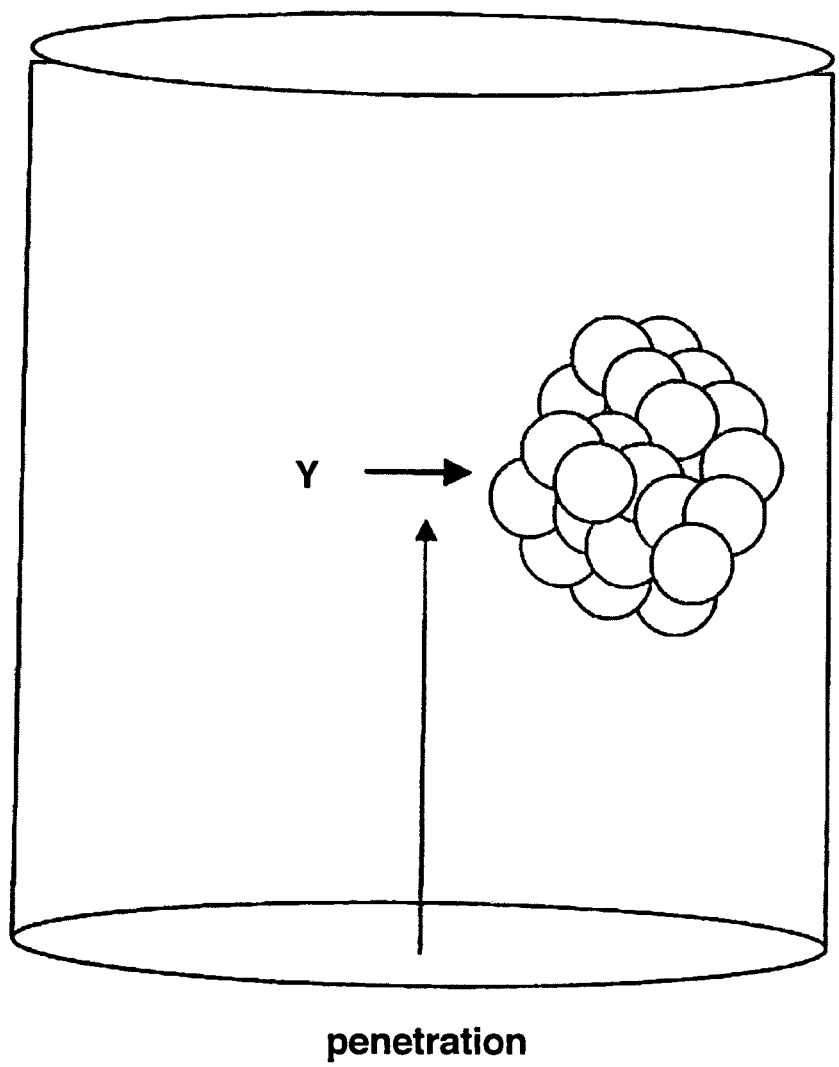

Strategies to use small quantities (5-20 mCi) of Bi-213 on labeled ligands have been proposed to kill individual cells such as cancer cells. This strategy involves the use of single doses of Bi-213 labeled antibody or other ligands. However, these methods alone do not enable the use of alpha particle emitting constructs because they fail to take into account the necessity for high specific activity ligands in order for specific cell kill to occur. This necessity arises from the particular nature of the alpha particle emission, that is, high linear energy transfer and extremely short range, which does not exist for the beta or gamma emissions that have been used therapeutically in humans. As a consequence, whereas a beta emitting therapeutic antibody that kills in a field of radiation may be effective at any number of specific activities, an alpha-emitting antibody will only be effective if a minimum of one atom can be delivered to each cell. In order to calculate the specific activity required (atoms of isotope per ligand molecule (or mCi per mg)), an understanding of (1) the target site number and (2) modulation and pharmacology of the ligand is required. Site number alone may differ over 1000 fold between different systems. As an example of the wide ranges of target site and ligand characteristics see Table 1:

TABLE 1

| Target | No. of sites per cell | Ligand Affinity |
| --- | --- | --- |
| Growth factor receptor on myeloid cell | 1000 | 0.1 nM (growth factor) |
| CD33 on leukemia cell | 10,000 | 1 nM (M195 IgG) |
| GD3 on melanoma cell | 1,000,000 | 10 nM (R24 IgG3) |

The minimum requirements to achieve reliable cell killing depend on: (1) the number of receptor targets (binding sites) on the target cell; (2) the stability of the ligand at the site once targeted; (3) the rapidity by which the ligand reaches the target site; (4) the affinity of the ligand for its target; and (5) the total number of target sites or non specific binding sites in the host (patient). With approximations of each of these features it is possible to estimate the specific activity necessary to make an effective agent in each therapeutic application. For example, if one Bi-213 disintegration, with a T½ of 46 min, is necessary to achieve single cell kill, and the radioactive ligand is stable at the cell for at least 3 hours, and 50% of the decays are in the wrong direction and expend their energy outside of the cell, and it requires 23 minutes for the ligand to reach the cell after injection and 23 minutes to prepare the manufactured dose and administer it into the patient, and there are 10,000 binding sites per cell, then a minimum of 1 out of every 2500 ligands must be labeled with a Bi-213 atom at the time of the end of the reaction to produce the radioligand. That is, at time=0 there is 1 Bi atom for each 2500 IgG; at time=46 minutes there is 1 atom for each 5000 IgG. Since there are 10,000 possible sites per cell, then 2 atoms will reach the cell and over 3 hours one will decay with an alpha into the cell and one, away from the cell, on average.

This is a rough estimate of the conditions for treating a leukemia with Bi-213 labeled HuM195 IgG (see example of its successful use in humans below). Thus, a minimum specific activity of about 10 mCi/mg is necessary. Since there is a range of 1-50E10 possible target leukemia cells (i.e. 0.1-5 E15 binding sites at 10,000 sites per cell) depending on the stage of disease, and about 50% of the antibody ultimately binds the target cell due to its affinity, a dose range of 0.05-2.50 mg of antibody is needed to saturate all the available binding sites and deliver an adequate dose. In contrast, for a ligand with similar pharmacology and preparation time, but 10 fold less sites, e.g. a typical cell surface receptor, a specific activity of nearly 1 atom per 250 ligands is required. If this were an IgG, then approximately 100 mCi per mg is necessary. Failure to use this level of specific activity would result in most cells receiving no radioactive atoms and hence an inability to adequately kill the target as compared to normal tissues. Thus, a minimum adequate specific activity of the radioactive construct is an integral characteristic of its description. Without this feature described it is not possible for someone skilled in the art to prepare a useful dose. Note that this concept is not necessary for use of an "immunotoxin" because in this case each IgG is labeled with a toxin molecule; moreover, the concept is not necessary for use with ligands labeled with beta emitters, I-131 or Y-90, etc., since these isotopes kill in a large field rather than at the individual cell level. Therefore this concept is unique and not previously described for radioimmunotherapy.

A second important concept is the relationship between the specific activity and the tumor control probability. The radiobiological issues associated with radioimmunotherapy of micrometastases are critical to proper treatment design and to the interpretation of clinical results. The initial criterion for effectiveness is much more difficult to meet in targeting micrometastases than it is in the treatment of measurable, bulky disease. In bulky disease, the initial criterion for effectiveness is the attainment of a complete response. If one assumes that the limit of detectability in a patient is 1 gram or $10^9$ cells, a complete response of a 100 gram lesion requires two logs of cell kill. Once adequate cell kill has been achieved, remission depends on the duration of the eradication. Durable remissions are much more difficult to achieve. In the adjuvant treatment of micrometastases, the remission duration will be the primary measure of effectiveness. This will depend upon the fraction of cells surviving after radioimmunotherapy and also on the time required for the population of cells to double when cell loss is negligible, i.e., the potential doubling time. The potential doubling time of most tumor cells ranges from 2 to 15 days (21). If the initial treatment yields a complete remission by reducing the tumor mass from 100 gm. to 0.1 gm, which is 3 logs of cell kill, and if the potential doubling time of the tumor cells is 15 days, then in about 2 months the tumor will have re-grown to 1 gram and the first evidence of a recurrence will be apparent. If adjuvant treatment yields another 3 logs of cell kill, following the initial 3 logs of kill, then $10^5$ tumor cells will remain. Assuming, a potential doubling time of 15 days, approximately 7 months will be required before the tumor becomes detectable. If only a single cell survives after adjuvant treatment, a recurrence may be expected in 15 months.

To achieve a cure, i.e., 5-year disease-free survival, the probability of killing all tumor cells must approach 1. This probability is equivalent to the tumor control probability (TCP) and may be calculated from: $TCP = e^{-n*SF}$ where n is the initial number of tumor cells, SF is the surviving fraction after treatment and e is Euler's number (2.71828 . . . ). If, for example, following surgery or radiotherapy $10^5$ tumor cells remain and these are reduced to a single cell (n=$10^5$; SF=$10^{-5}$) then the probability of tumor control is 0.37. An additional log of cell kill increases the control probability to 90%; 99% probability is achieved after 7 logs of cell kill. Four logs of cell kill, which would reduce the tumor cell number from $10^5$ to 10 cells, only yields a tumor control probability of 0.005%. In clinical terms, 37% of patients with $10^5$ tumor cells would achieve a 5-year disease-free survival if treatment potency was such that $10^5$ tumor cells could be reduced to 1 tumor cell. If the treatment were potent enough to reduce $10^7$ cells to a single cell, 99% of patients with $10^5$ cells would be disease-free after 5 years. If, in the same patient population, treatment reduced the total number of cells to 10 from $10^5$, only 5 in every 100,000 patients would be cured.

Although the analysis presented above is a simplification that ignores a large number of factors that are operative in determining the time to recurrence and the probability of cure, the exercises highlight the fundamental differences between the criterion used for evaluating an agent against measurable versus micrometastatic disease and between remission and a durable remission/"cure". As is evident from the analysis, the number of tumor cells remaining in the patient after treatment of the primary or observable metastases will be a critical determinant of efficacy.

All previously described alpha-emitting constructs were of such low specific activity that construction of ligand to their specifications would have yielded ineffective agents or agents unable to induce cures when injected into humans. Moreover, the consequences of this low specific activity were unrecognized until the work described here because the field had relied exclusively on the use of beta and gamma emitters, and because no one had ever successfully scaled up targeted alpha emitters for human use.

Besides Bi-213, a long-lived ($t_{1/2}$=10 days) alpha-emitting radionuclide Ac-225 is also investigated. Ac-225, with 3 alpha-emitting daughters, should be far more potent than the short-lived ($t_{1/2}$=46 min.) alpha-emitting Bi-213 in killing individual cells, if it retained in or on the cell, and multicellular spheroids, if it can penetrate into the spheroid over time. These features of Ac-225 may allow for alpha therapy of solid tumors; Bi-213 is unlikely to be useful for treating solid tumors unless multiple doses of drug can be used to slowly "peel away" layers of tumor cells. The respective pros and cons to using Ac-225 and Bi-213 are shown in Table 2.

target cell by modulation into a cytoplasmic compartment, will yield a drug that is even more potent, i.e., as much as 1000 fold more on a mCi basis, than Bi-213 constructs. Moreover, the long half-life will allow targeting of solid tumors and larger micrometastatic lesions than are possible with the short-lived Bi-213. Possible target systems under study include the breast and prostate models. Total doses of less than 1 mCi are envisioned.

In the present invention, high specific activity alpha-emitting constructs are disclosed. Further, methods of killing large tumors or other cells involved in human or animal diseases using the alpha-emitting constructs are also disclosed.

The present invention is directed to a method of killing a large tumor comprising the step of administering multiple doses of an alpha-emitting construct to the tumor. Specifically, the tumor is larger than 1 mm in diameter. Preferably, the alpha-emitting construct comprises an antibody, a fragment, a cytokine, a receptor ligand and other such ligands. Representative examples of alpha-emitting isotopes include Bismuth-213, Bismuth-212, actinium-225, radium-223, lead-212, terbium-149, fermium-155 and astatine-211. Generally, the construct has a high specific activity of from about 0.1 mCi/mg to about 50 mCi/mg. That is, the construct is administered in a dose adequate to deliver a minimum of 1 atom per cell. Preferably, the alpha-emitting construct is administered by repeated dosing in a range of from about 0.1 mg/m$^2$ to about 10 mg/m$^2$.

The present invention is also directed to a method of killing a non-malignant cell involved in a human or an animal disease comprising the step of administering an alpha-emitting construct to the cell. Representative examples of alpha-emitting construct include antibodies or fragments thereof, a cytokine, a receptor ligand and other such ligands. Representative examples of alpha-emitting isotopes include bismuth-213, bismuth-212, actinium-225, radium-223, lead-212, terbium-149, fermium-155 and astatine-211. The construct is highly specific with the activity of from about 0.1 mci/mg to about 50 mci/mg and administered in an effective dosage of from about 0.1 mg/m$^2$ to about 10 mg/m$^2$. That is, the construct is administered in a dose adequate to deliver a minimum of 1 atom per

TABLE 2

Pros and cons of Ac-225 vs. Bi-213 use clinically

| Pro: Ac-225 | Con: Ac-225 | Pro: Bi-213 | Con: Bi-213 |
|---|---|---|---|
| Long $t_{1/2}$ = 10 days allows time to target and penetrate tumor | In vivo stability of chelate is unknown | Short $t_{1/2}$ = 46 min. means no long term residual activity | Targeting must be rapid |
| Daughters may yield more alpha particles and improve therapy | Daughters may leak from target and kill nonspecifically | No long lived daughters | Single alpha emission |
| Active agent might be formulated and dispensed from a central pharmacy | | | Active agent must be prepared on site for rapid use in clinic |
| Microcurie levels of activity (relative to Bi-213) required | | | |

Using IgG-chelate constructs of relevant and control mAbs labeled with Ac-225, the potency and specificity of Ac-225 labeled constructs are investigated in killing tumor cells and spheroids in vitro. The role of the constructs in cellular internalization and catabolism, and retention of the nuclide in the cells are also evaluated.

It is hypothesized that generation of alpha-particles in vivo, at the target site, by targeting a long-lived isotope that decays via 4 alphas, which may be bound and retained within the cell. Representative examples of non-malignant cells that can be treated using this technique include virus-infected cells, autoimmune cells, lymphoid cells, normal bone marrow cells and abnormally proliferating normal cells. The individual may have a disease such as neoplastic disease, viral infection, autoimmune disease, prostatic hypertrophy, coronary disease and other vascular occlusive disease.

The present invention is further directed to a method of killing a tumor by targeting antigens in the tumor vasculature of an individual in need of such of such treatment, comprising the step of: administering to said individual a pharmacologically effective dose of a construct comprising an alpha-emitting isotope effective to inhibit the function of said tumor vasculature. Representative examples of alpha-emitting constructs include antibodies or fragments thereof, cytokine, a receptor ligand and other such ligands. Preferably, the alpha-emitting construct is labeled by Bismuth-213, Bismuth-212, actinium-225, radium-223, lead-212, terbium-149, fermium-155 or Astatine-211. The construct is highly specific with the activity of from about 0.1 mci/mg to about 50 mci/mg and administered in an effective dosage of from about 0.1 mg/m$^2$ to about 10 mg/m$^2$. That is, the construct is administered in a dose adequate to deliver a minimum of 1 atom per cell.

As used herein, "specific activity of an alpha-emitting construct" refers to refers to the number of radioactive atoms per ligand molecule. As used herein, "tumor control probability (TCP)" refers to the probability that a tumor will be reduced to the size below which it can not recur. As used herein, "remission duration" refers to the time after treatment before the tumor recurs. As used herein, "doubling time" refers to time it takes for a cancer cell or tumor to double in size.

The following examples are given for the purpose of illustrating various embodiments of the invention and are not meant to limit the present invention in any fashion.

Example 1

Materials and Methods

Ac-225 is obtained from the European Institute for Transuranic Research, Karlsruhe, Germany or from the United States Department of Energy (Oak Ridge, Tenn. or Hanford, Wash.). Approximately 20-25 mCi of Ac-225 residue was dried onto the inner surface of a glass ampoule that is attached with 1/32 inch diameter tubing to a 5 cm by 0.5 cm polypropylene tube with barbed reducing fittings, sintered polyethylene plugs, and some acid washed glass wool containing approximately 200 mg of dry AG MP-50 resin, 100-200 mesh, H$^+$ form (BioRad Laboratories, Hercules, Calif.). The ampoule and column are disconnected, and the ampoule fitted with two 3-way stopcocks. The residue in the glass ampoule was exposed to 0.5 ml of 3 M Optima grade HCl (Fisher Scientific), added with a 3 ml syringe through one of the stopcocks. The other end of the glass ampoule containing the Ac-225 acid solution was vented to the atmosphere using a 0.22 mm filter (Corning) allowing release of any pressure increase due to heat or gas generation. The 3 M acid is allowed to contact the residue in the glass ampoule for 1 hour with mild agitation to completely dissolve all of the Ac-225. After 1 hour a second syringe containing 0.5 ml of metal free water was attached, via the stopcock, and the acidic actinium chloride solution carefully diluted. The resulting 1.5 M acidic solution of actinium was withdrawn into the syringe, the ampoule carefully disconnected and the syringe with the Ac-225 solution attached to the ampoule.

The resin in the column was washed with 10 ml of 1.5 M Optima grade HCl, the resin was removed by backwashing and 100 mg was placed into a clean 10 ml syringe in 2 ml of 1.5 M Optima grade HCl solution. Of the remaining 100 mg of washed resin, 50 mg was loaded back in the column and a small piece of acid washed quartz glass wool added to hold the resin in place. This 50 mg section of resin serves as a catch plug to capture any Ac-225 that might break through during routine elution. The column, the syringe with the Ac-225 solution, and the 10 ml syringe were all attached via a 3-way plastic stopcock. The exit end of the column was attached to a 60 ml syringe that will be used to apply a negative pressure while filling the column.

Manipulation of the 3-way stopcock allows the Ac-225 solution to be pulled into the syringe containing the AG MP-50 resin slurry. This Ac-225 solution and resin slurry were allowed to contact for 30 min. with occasional gentle agitation. After batch loading the Ac-225 onto the resin support, the 3-way stopcock was again manipulated to load the Ac-225/resin into the column. The apparatus was positioned so that the column now stands vertically to allow the Ac-225/resin to flow downward. The resin was gently mixed prior to pulling it out of the 10 ml syringe with a slight negative pressure to pack the column. The stopcock position originally used for the syringe with the Ac-225 solution was now attached to a clean syringe with 10 ml of 1.5 M Optima grade HCl washing solution. This wash was pulled into the 10 ml syringe where the resin was loaded, agitated slightly to rinse the syringe, and then used to wash the generator column. The 60 ml syringe was used to pull the wash solution through the column. The column was disconnected from the 3-way stopcock and a small plug of acid washed quartz glass wool is applied to hold the resin in place. A layer of 50 mg of resin was further added to serve as the second catch plug which is utilized when the column flow is reversed. A small piece of acid washed quartz glass wool was again added and the column completed by the addition of a barbed reducing fitting. The generator was then ready to use. It is recommended to vertically position the generator when eluting so that the catch resin portion is always on top thus allowing any fines produced to settle out and not clog the resin.

A 0.1M HCl/0.1M NaI buffer is prepared fresh each time and used to elute Bi-213 from the resin. The Bi-213 reaches secular equilibrium with the Ac-225 after approx. 138-300 minutes (6.5 Bi-213 $t_{1/2}$'s). 2.5 ml of 0.1M HCl/0.1M NaI elution buffer was required to elute 98% of the recoverable bismuth and 3.6 ml elutes all of the recoverable bismuth. A freshly prepared 0.1M HCl/0.1M NaI solution is colorless, however after passage over the generator resin, it elutes as a faint yellow colored solution. Addition of 0.20 ml of 3M ammonium acetate was required to buffer 3.6 ml of 0.1M HCl/0.1M NaI eluate to pH 4-5. A 150 mg/ml solution of l-ascorbic acid was prepared in metal free water and batch reacted with Chelex-100 resin for twenty minutes. After twenty minutes, the l-ascorbic acid/Chelex 100 slurry is filtered through a 0.45 mm filter and the metal free l-ascorbic acid eluate collected. A volume of this eluate is added to the buffered Bi-213 mixture to yield a final concentration of l-ascorbic acid equal to 5 mg/ml. The antibody construct, CHX-A-DTPA-HuM195, was then added to the buffered Bi-213 solution and incubated at room temperature for up to 20 minutes. Reactions taking greater than 4 minutes typically result in a greater loss of Bi-213 product due to decay than allowing the reaction to proceed longer and increasing product yield. Following this incubation, 0.020 ml of 10 mM EDTA solution was added to quench the reaction mixture and chelate any free, reactive radiometal ions. Quenching was necessary because the reaction with the desired carrier may not proceed quantitatively (Bi-213 incorporation >98%) to desired product. In addition, a means of separating product from reactants and byproducts is also needed. The radiolabelled antibody was purified from low molecular weight impurities rapidly by size exclusion chromatography.

Example 2

IgG

HuM195 (Protein Design Labs, Inc., Mountain View, Calif.) is a recombinant IgG1 mAb that was constructed by combining the CDR regions of the murine M195 with human framework and constant regions. Both M195 mAbs bind with high affinity to the CD33 antigen (22-26). The J591 antibody, which is reactive with the Prostate Specific Membrane Antigen (PMSA) on prostate cancer cells, was the gift of Dr. Neil Bander at New York Hospital.

Example 3

Conjugation of Chelate to IgG

HuM195 was conjugated to 2-(p-SCN-Bz)-cyclohexyl-DTPA (CHX-A-DTPA), a recently developed backbone substituted derivative of DTPA24, using a single vessel method (27) or conventional methods (28). The average number of chelates per antibody ranged from 5 to 10.

Example 4

Radiolabeling

Bi-213: the radionuclide generator used for low activity level Bi-213 production is described elsewhere (15, 29). The construction of generators capable of producing 10-25 mCi of Bi-213 required several modifications. The generator was washed with 0.001 M HCl and then eluted with 0.5 to 1 ml of 0.1 M HCl, 0.1 M NaI to elute Bi-213. For radiolabeling of protein, the eluate was brought in the range of pH 4-4.5 with 3 M ammonium acetate and immediately used as described for Bi-206. Bi-212: Bismuth-212 was eluted from Ra-224/Bi-212-generator 14 and HuM195 was labeled under similar conditions as described for Bi-213.

Example 5

Bi-213 Counting

Bi-213 radioactivity (photon energy 440 KeV, 28% abundance) was quantified using a Squibb CRC-17 Radioisotope Calibrator at a fixed setting that was standardized using a Canberra multi-channel pulse height analyzer. A Packard Cobra gamma counter (340-540 KeV window) was used to determine the relative number of Bi-213 counts in ITLC, ATLC, HPLC, Protein A, and cell samples. Other nuclides were counted using standard methods.

Example 6

Purification of Radiometal Chelate-Conjugated IgG

Radiolabeled CHX-A-DTPA-HuM195 constructs were purified either by high-performance liquid chromatography (HPLC) using a Bio-Sil-250 size exclusion column (600×7.5 mm) with 20 mM sodium acetate/150 mM sodium chloride, pH 6.5 mobile phase or by using low pressure chromatography employing a 10 DG size exclusion column (Bio-Rad Laboratories, Inc., Hercules, Calif.) with a 1% human serum albumin/0.9% sodium chloride mobile phase.

To determine the labeling efficiency and purity of the reaction mixture and final product, a 5 ml sample was removed for instant thin layer chromatography (ITLC) (Gelman Science Inc., Ann Arbor, Mich.) 32. The plates were developed with 10 mM EDTA. Under these conditions, mAb remains at the origin and free metal migrates with the solvent front. The strips were cut at rf=0.5 and counted in a gamma-counter.

Example 7

Conjugation of HuM195 to CHX-A-DTPA

HuM195 CHX-A-DTPA labeling efficiency with Bi-213 was typically over 90% at specific activities of up to 20 mCi/mg, but efficiency decreased in direct relationship to the specific activity desired. With specific activities of 50 mCi/mg, 50-70% efficiencies were achieved. This reduction may have been due to the small amounts of antibody used to achieve the higher specific activities. The chelation reaction ran to near completion (85%) in 6 min., but was allowed to continue for a full 15-20 min. to optimize labeling. However, because of the short half-life of Bi-213, continuing the reaction beyond about 5 min. does not increase final yield of labeled product as product is lost through decay. These labeling efficiencies were comparable to those seen with In-111, Bi-206 and Bi-212 using the CHX-A-DTPA-HuM195 construct.

Conjugation of HuM195 to CHX-A-DTPA resulted in the attachment of up to 10 ligand molecules per antibody. High chelate to protein ratios did not significantly affect the immunoreactivity. The immunoreactivity of the metal-labeled CHX-A-DTPA-HuM195 varied from 80% to 95% and was independent of the specific activity. This is consistent with the amino acid sequences in the CDR regions of the HuM195 (30).

Example 8

Immunoreactivity

The immunoreactivity of the bismuth labeled CHX-A-DTPA-HuM195 constructs was determined as described by incubating 2 ng of radiolabeled mAb in 30 ml total volume with a 20- to 30-fold excess of antigen (10×106 or 15×106 CD33 positive HL60 cells). These cells have approximately 10,000-20,000 CD33 positive binding sites per cell and have the capacity to bind up to 90% of added HuM195). After incubation, the cells were collected by centrifugation and unbound IgG was removed to a second set of the cells and reincubated with the same amount of excess antigen as in first incubation for 90 min. at 0° C. Under these conditions of large antigen excess in a small volume, the reaction goes to near completion in 60 minutes. The percentage immunoreactivity was calculated as equal to (bound Bi-206-IgG to cells #1 plus cells #2)/(total bound plus unbound Bi-206-IgG) times 100. Specific binding in these radiobinding assays was confirmed by lack of binding of the radiolabeled mAb to CD33 negative RAJI cells. To avoid nonspecific and Fc receptor binding, the assays were performed in the presence of 2% human serum.

A rapid, affinity thin-layer chromatography (ATLC) assay was implemented to measure the immunoreactivity of the short-lived Bi-213 constructs (31). The immunoreactivity was assessed as the percent radiolabeled construct bound to the portion of the paper strip containing the target antigen which was prepared from extracts of AL67 cells (CD33 transfectants).

Example 9

Modulation of Cell Surface Antibody-Antigen Complexes

Internalization of the cell surface antibody antigen-complex was measured by incubating 0.5 mg/ml of radiolabeled mAb with $5 \times 10^5$ cells over time at 37° C. Cell pellets were washed twice in RPMI, and then surface-bound (Bi-206) CHX-A-DTPA-HuM195 was stripped with 1 ml of 50 mM glycine/150 mM NaCl, pH 2.8, at 24° C. for 10 minutes. Total cell-associated radioactivity and acid-resistant (internalized) radioactivity were determined. To avoid nonspecific and Fc binding, the assays were performed in the presence of 2% human serum.

Example 10

Cell Killing

The potency of (Bi-213)CHX-A-DTPA-HuM195 and (Bi-212)CHX-A-DTPA-HuM195 for killing of leukemia cells was measured using 2×105 HL60 cells (CD33+) or RAJI cells (CD33−) in 100 ml in 96 well plates. Serial dilutions of bismuth labeled antibody were added to the wells to yield final activity in the wells ranging from 0.02 to 20 mCi/ml. The experiments were done with different specific activities of the bismuth antibody (3 to 20 mCi/mg). The plates were incubated 24 h at 37° C. in 5% CO2. After incubation, cell viability was determined by $^3$H-thymidine incorporation. To avoid nonspecific and Fc receptor binding during incubation, the assays were performed in the presence of 2% human serum.

In addition, a bifunctional chelate, labeled to high specific activity, was conjugated with an alpha-emitting isotope. Internalization, high immunoreactivity, tumor cells kill in vitro, the relationship between cell kill and specific activity was demonstrated with a total of 5 different monoclonal antibodies: HuM195 humanized anti-CD33 to myeloid leukemias, C2B8 chimeric anti-CD20 to lymphomas, J591 mouse anti-PSMA to prostate cancer, mouse SJ25C1 and mouse B4 anti-CD19 to B cell leukemia and lymphoma. Thus, multiple examples with mouse, human, and chimeric antibodies in several tumor antigen systems have been documented.

Example 11

Specific Cytotoxicity

Killing of Large Tumor Clusters In Vitro

FIG. 2 demonstrates, in a spheroid model, the possibility of killing larger tumors by repeated dosing. As may be seen in the figure, a single dose has eliminated 5 to 6 layers of cells, leaving behind a previously unexposed "core" of cells that can then be targeted by a subsequent administration. In contrast, spheroids of the same cell line, exposed to a Bi-213-labeled irrelevant antibody, continue to grow exponentially. These results are in contrast to the observations of Langmuir et al. (14), upon investigation of Bi-212-labeled antibody targeting of large spheroids, concluded that due to their short half-life and range of the alphas, alpha-emitters would not be effective against larger tumors because of the time required for antibody penetration. FIG. 2 illustrates that this will not be a limiting factor if repeated dosing is used.

Figure 3A:
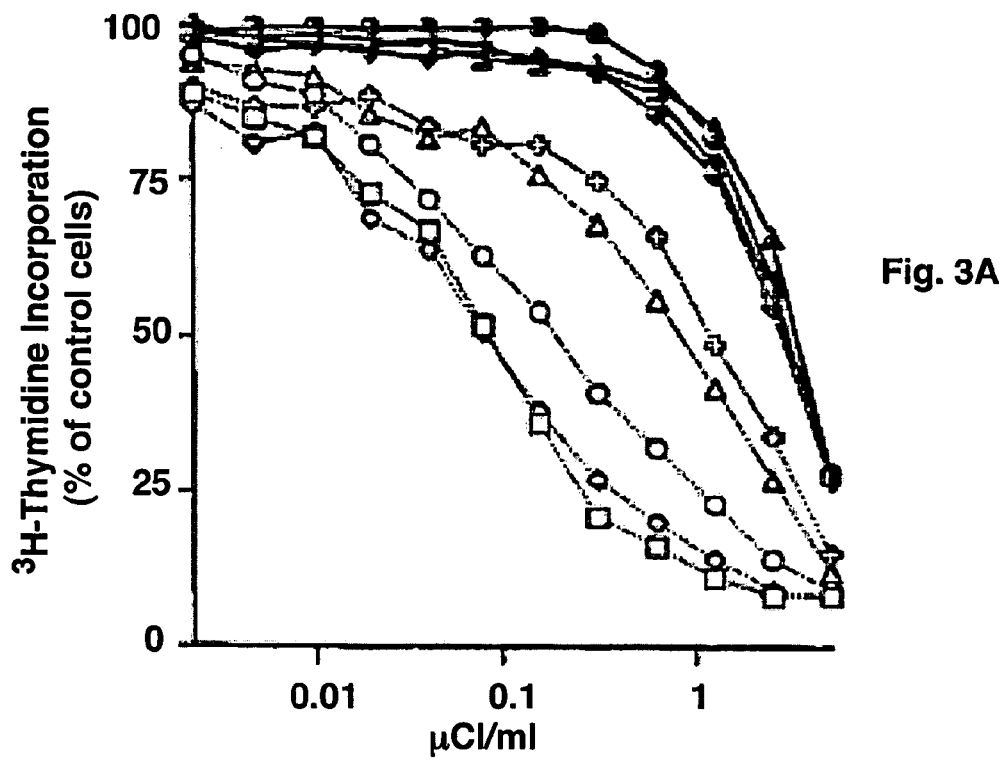
FIGS. 3A-3B show the potency of (Bi-213)CHX-A-DTPA-HuM195 and (Bi-212)CHX-A-DTPA-HuM195 at killing leukemia cells in vitro. Cytotoxicity was measured using HL60 cells (CD33+) (dotted lines) and RAJI cells (CD33−) (solid lines) using specific activities ranging from 0.2 mCi/mg to 30 mCi/mg. 2×10$^5$ cells in 100 ml were placed in 96 well plates. Bismuth labeled antibody was added in the wells in serial dilution so that final concentrations in the wells were in a range of 0.02 to 20 mCi/ml. The plates were incubated 24 h at 37° C. in 5% CO2. Viability was determined by 3H-thymidine incorporation, and is plotted against specific activity.

Cell killing experiments with different specific activities of Bi-212 or Bi-213 labeled CHX-A-DTPA-HuM195 showed dose- and specific activity-dependent killing of CD33+ HL60 cells. (Bi-212)CHX-A-DTPA-HuM195 was at least 10 times more potent at killing CD33+ HL60 cells as compared to CD33 negative RAJI cells at 24 hours in in vitro assays (FIG. 3A). The potency against the specific target HL60 cells depended directly on the specific activity, i.e., the number of Bi-212 per IgG molecule, of the labeled antibody with the highest specific activities (30 mCi/mg) showing the highest potency. As specific activity was decreased there was a loss of selective cell killing. Potency for killing HL60 cells at a specific activity of 0.2 mCi/mg approached the potency for killing the RAJI control cells.

The dependency of selectivity on specific activity can be explained by examining the number of CD33 target sites on each HL60 cell and the number of bismuth atoms labeled per HuM195 IgG molecule. At 0.2 mCi/mg, only about one IgG out of 100,000 contains a Bi-212. Because there are only 10,000 CD33 sites per cell, it is unlikely that specific cell killing can occur. Nonspecific cytotoxicity from alpha particle radiation in the media, or from antibody constructs nonspecifically bound to the cells then dominate the cytolytic activity. Thus, killing of HL60 cells at low specific activities of labeling approached that of RAJI. Conversely, at specific activities of 20 mCi/mg, about one out of 1000 HuM195 IgG molecules are labeled, thus allowing a mean of ten Bi-212 atoms to be delivered to each HL60 cell at saturation. Therefore, at high specific activities, cytotoxicity should depend directly on the binding characteristics of HuM195 for HL60 cells. The binding isotherm displays exponential increase in binding from 10 to 1000 ng/ml. Nonspecific binding shows linear increases, beginning at higher concentrations.

Figure 3B:
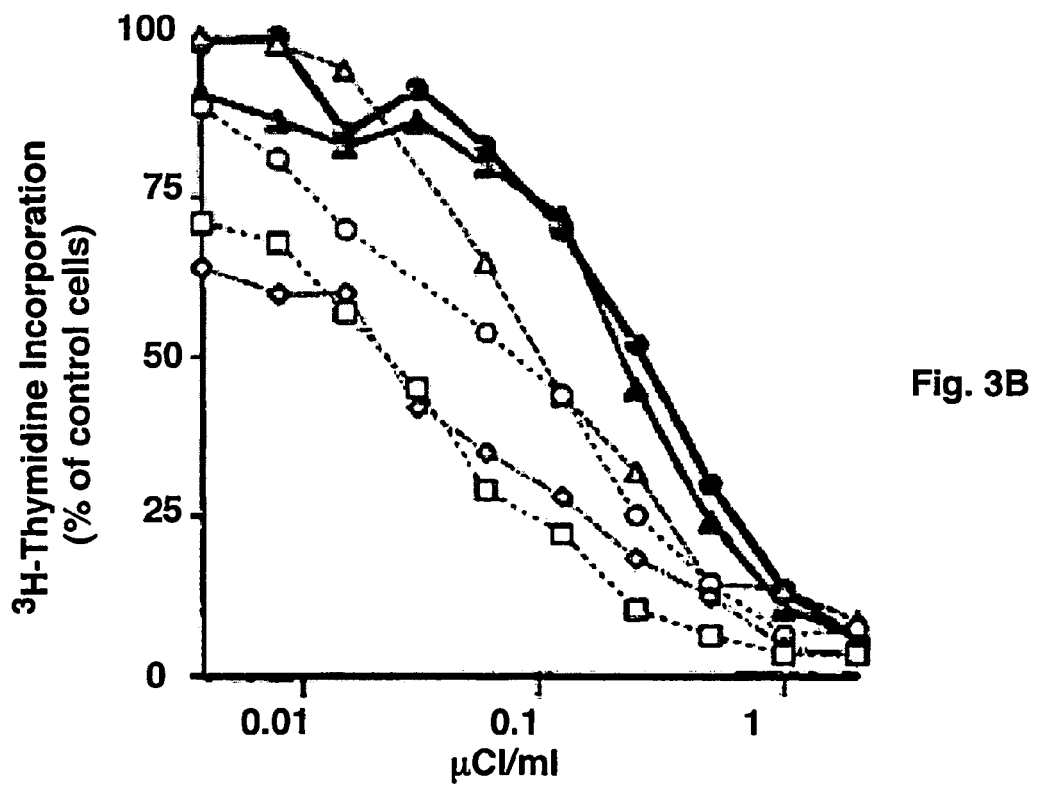

Similar specific killing of HL60 cells was observed for (Bi-213)CHX-A-DTPA-HuM195 (FIG. 3B). At specific activities of 8-10 mCi/mg, potency against HL60 cells was about 10 fold higher than against RAJI cells. As expected, (Bi-212)CHX-A-DTPA-HuM195 was slightly more potent than (Bi-213)CHX-A-DTPA-HuM195; this is because at the same specific activities, more Bi-212 would be conjugated per HuM195 IgG due to its longer physical half-life. Therefore, for equivalent binding of HuM195 to each cell, more alpha decays would be delivered by Bi-212-constructs. As with Bi-212, the potency of cell kill depended directly on the specific activity of bismuth atoms per IgG, as well as on the total dose added.

Figure 4A:
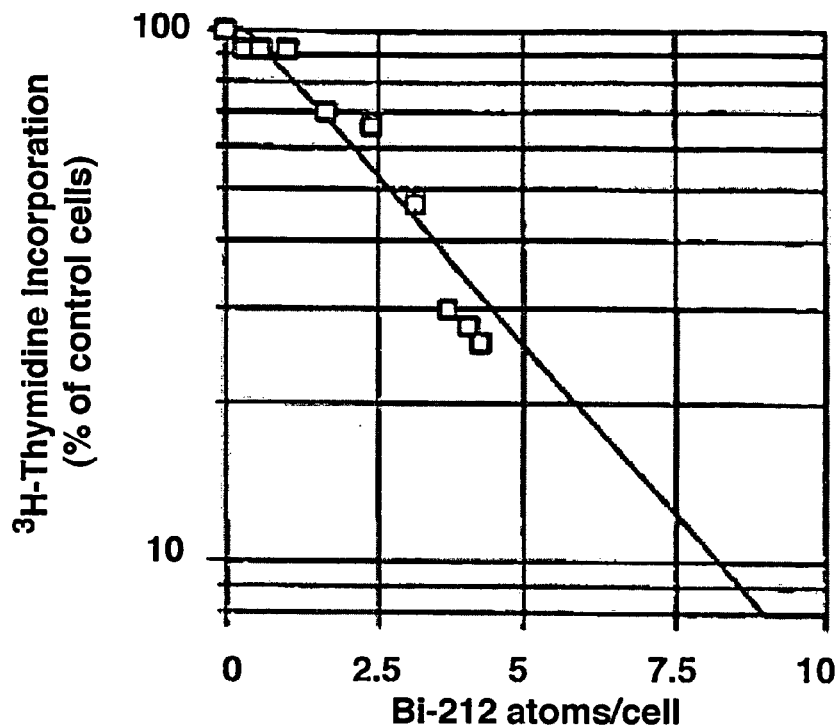
FIGS. 4A-4B shows HL60 cell viability as a function of the calculated average number of Bi-213 atoms (FIG. 4A) and Bi-212 atoms (FIG. 4B) bound on the cell surface. The line represents a linear best fit for the cytotoxicity data points taken from bismuth labelings that yielded a specific activity of about 10 mCi/mg. This specific activity is in the region of highly selective killing of HL60 cells. Curves of similar slope can be generated from cytotoxicity data at other high specific activities (not shown).
Figure 4B:
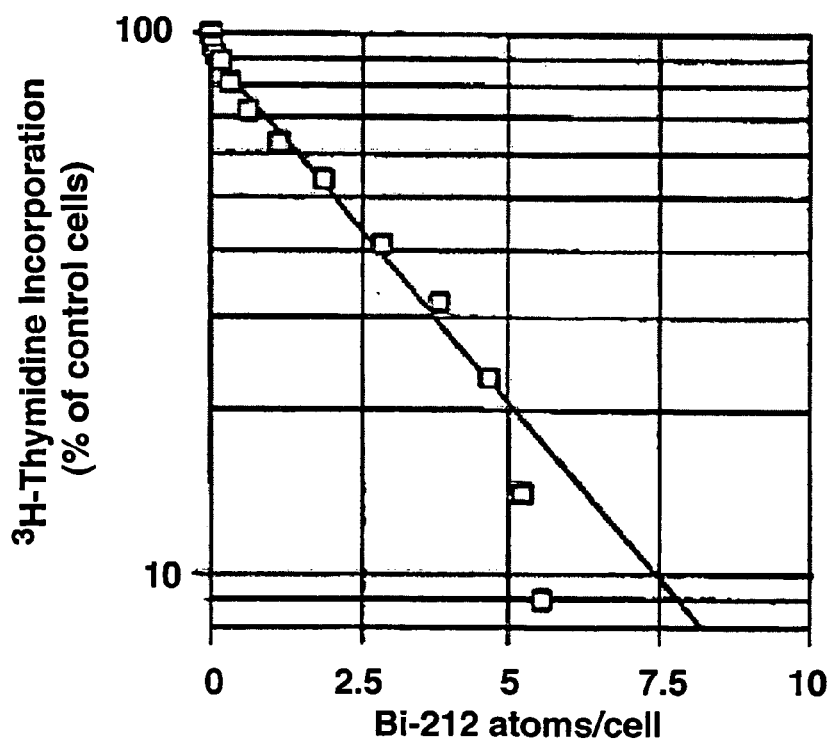

In order to determine the number of bismuth atoms necessary to specifically kill HL60 cells, the cytotoxicity data were replotted as a function of bismuth atoms per cell (FIG. 4). Data for killing at a specific activity of 10 mCi/mg are shown. The HL60 cell viability was a function of Bi-212 and Bi-213 atoms bound on the cell surface. To calculate the initial amount of bismuth atoms bound on the cell surface, specific activity and Scatchard analyses were used to estimate the percentage of binding sites that are occupied with HuM195. The lines in FIG. 4 represent a best fit for the data points that are in the region of specific killing. This is described by the function $Y=111.24 \times e^{-\ln 2 \times 0.419 X}$ for Bi-213; where Y is viability and X number of initial bismuth atoms. The function is $Y=87.42 \times e^{-\ln 2 \times 0.429 X}$ for the Bi-212 labeled antibody constructs. These data yield an LD50 dose of Bi-213 and Bi-212 that is in the range of 2 to 2.5 initial atoms per cell.

Figure 5:
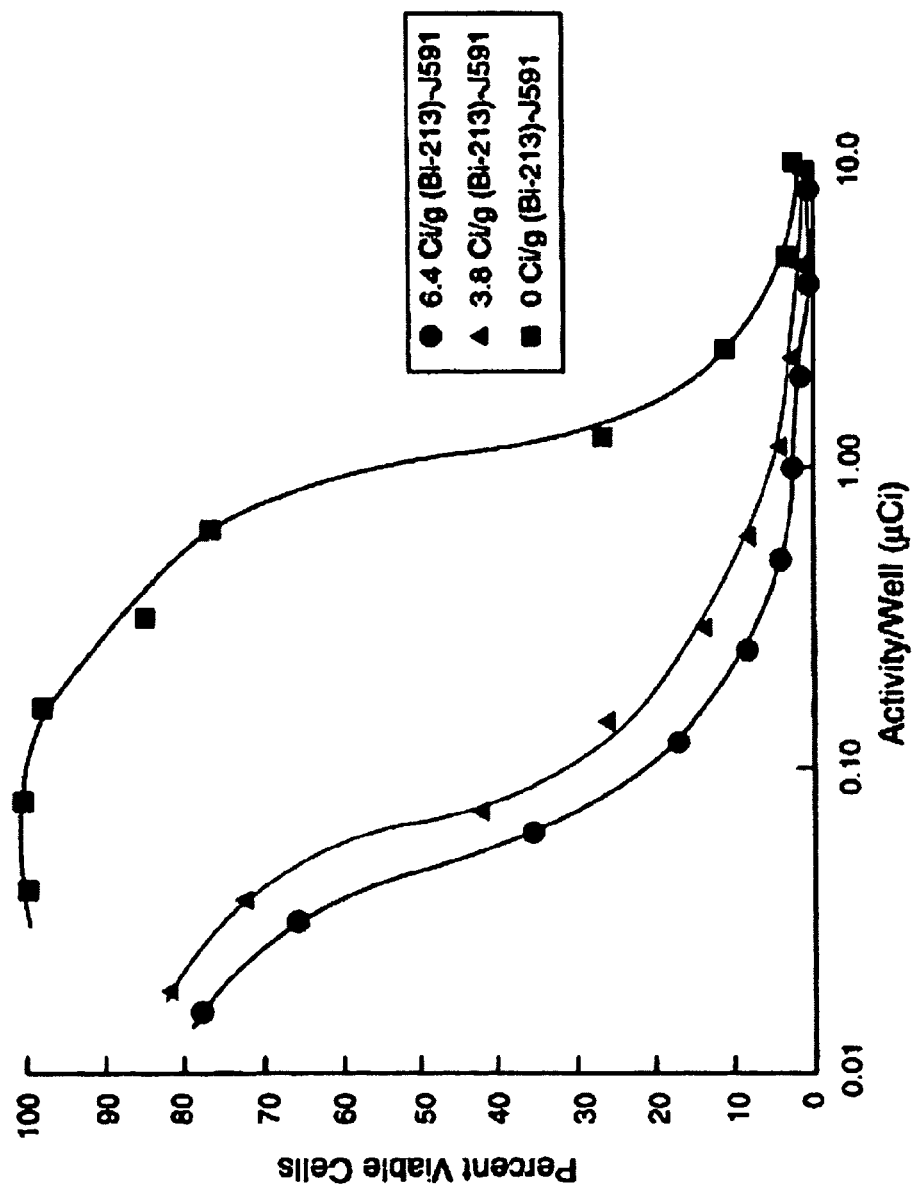
FIG. 5 shows the potency of Bi-213-J591 against LnCaP cell viability as a function of specific activity. As the specific activity is lowered, the ability of the same concentration of isotope to kill the target cells is reduced dramatically.

To show that specific killing was not a unique property of the leukemia system, similar experiments with Bi-213 labeled J591 antibody (Liu, 1997) and human prostate cancer cells (LnCaP cells) were conducted. The same dependence on specific activity in this system was observed (FIG. 5).

Example 12

Treating Macroscopic Animal Tumors

To demonstrate that alpha-emitting ligands have an effect on macroscopic tumors in vivo, an animal therapy study was conducted using nude mice injected with 15 million LnCaP prostate tumor cells into their thighs. Tumors were allowed to grow until visible and were 3-5 mm in diameter. One group of mice was then treated with the Bi-213 labeled J591 antibody specific for prostate cancer cells and one group received a control antibody at a slightly larger dose (Bi-213-HuM195). As a quantitative measure of antitumor activity, Prostate Specific Antigen (PSA) was measured in the serum of mice before and after treatment. One week after treatment, mice given the control antibody showed a mean 26% rise in PSA (n=4) whereas mice treated with the specific J591 antibody showed only a mean of 6% rise (n=4).

In a second experiment, 6 million prostate cancer cells were injected into mice. Mice were treated with a control Bi-213 radiolabeled antibody, no antibody, or Bi-213 labeled radioactive J591 prostate specific antibody. By 28-31 days, both control groups had evidence of cancer in 50% of the animals. In contrast, in the treatment group, it required 46 days before 50% of the animals showed tumors. Hence, the alpha-emitting prostate antibody was capable of slowing the growth of a macroscopic tumor. Other tumors that might be approached by such a method include "benign" tumors such as "benign prostatic hypertrophy" caused by neoplastic, but not malignant, overgrowth of the prostate. This condition afflicts millions of men worldwide.

Example 13

Cell Killing In Vivo by Bi-213 J591

Figure 6:
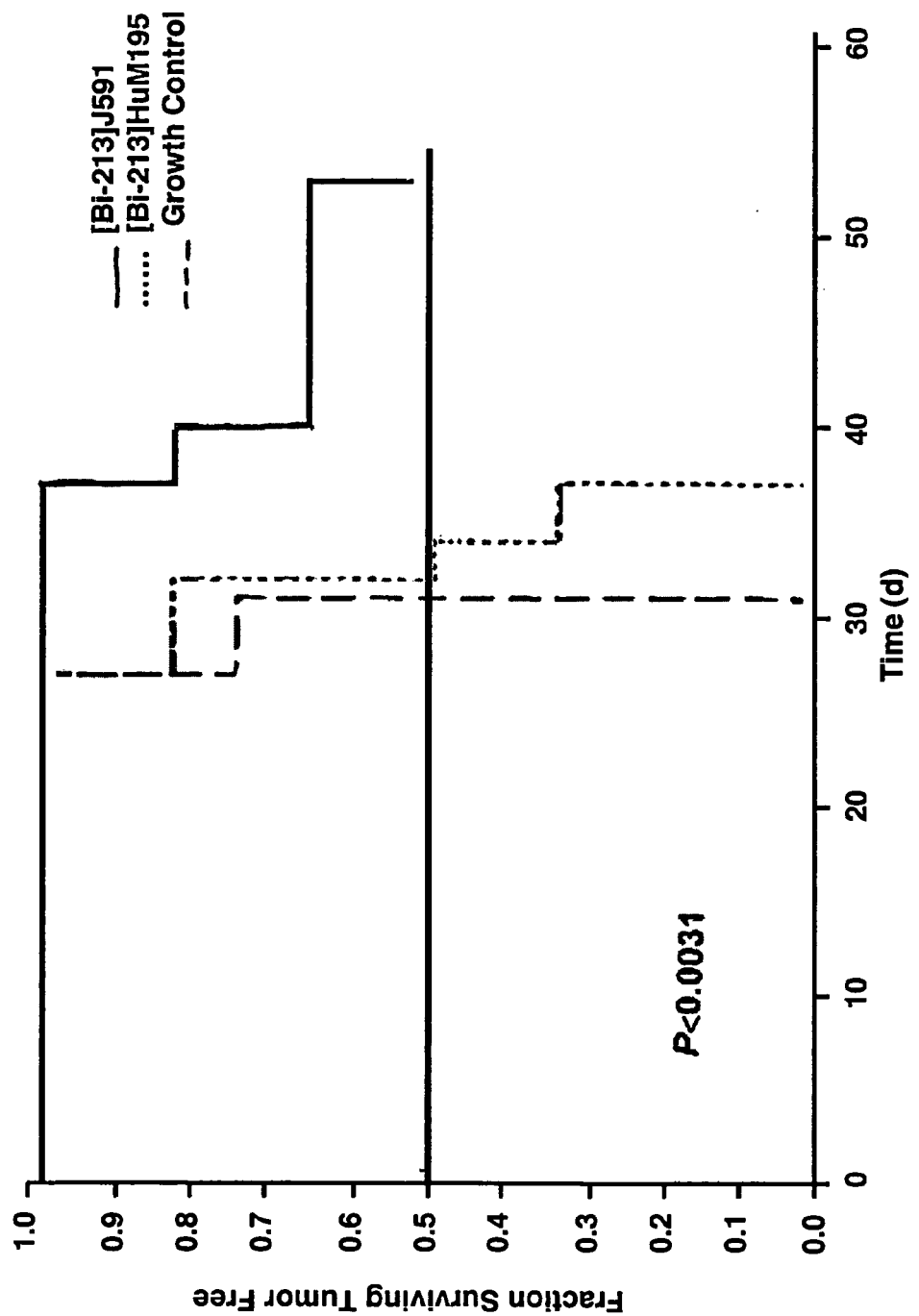
FIG. 6 shows Kaplan-Meier survival plot of fraction of mice surviving tumor-free vs. time for LNCaP xenografted mice treated with Bi-213-J591, Bi-213-HuM195, and an untreated growth control.

A single course of the Bi-213 J591 drug was administered to the LNCaP mouse model in four daily doses. The results show that median tumor-free survival of LNCaP xenografted mice was improved ($p<0.0031$) relative to mice treated with Bi-213-HuM195 or untreated controls (FIG. 6). The median tumor-free survival times were 31 days (n=4, untreated animals), 33 days (n=6, Bi-213-HuM195-treated animals), and 54 days (n=6, Bi-213-J591-treated animals).

Figure 7:
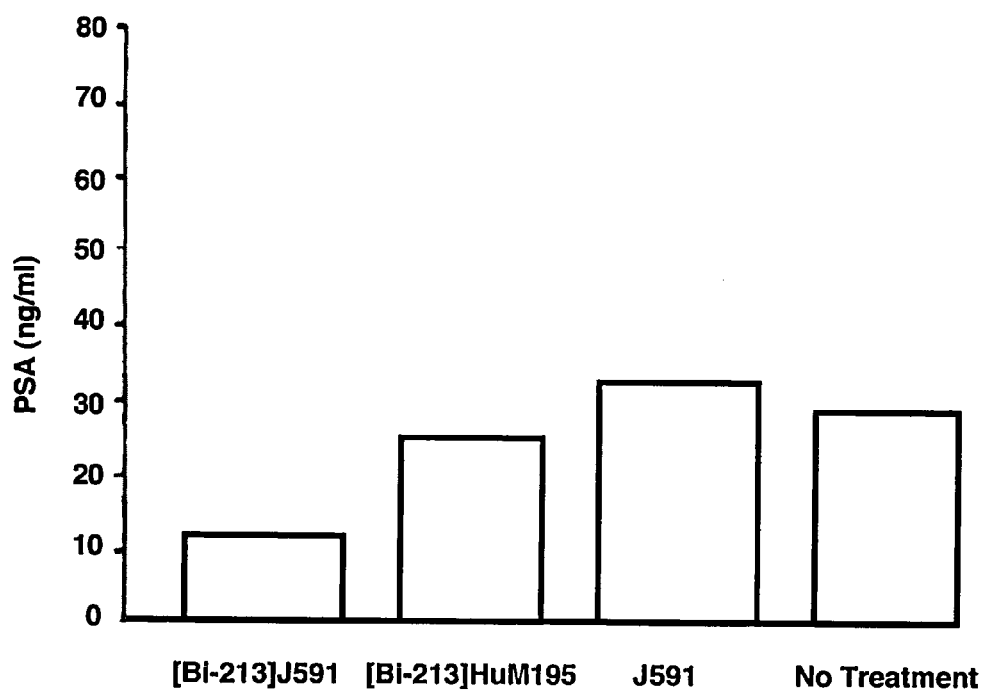
FIG. 7 shows mean PSA values at day 30 for LNCaP xenografted mice treated with Bi-213-J591, Bi-213-HuM195, unlabeled J591, and an untreated growth control.

PSA levels were also evaluated in tumor-bearing mice. It shows that the mice responded to the treatment (Table 3). Mean PSA values, 51 days after treatment, were 104 ng/ml±54 ng/ml (n=4, untreated animals), 66 ng/ml±16 ng/ml (n=6, Bi-213-HuM195-treated animals), and 28 ng/ml±22 (n=6, Bi-213-J591-treated animals). The reduction of PSA levels in mice treated with Bi-213-J591 relative to mice treated with Bi-213-HuM195 and untreated control animals was significant with $p<0.007$ and $p<0.0136$, respectively. In another similar experiment where unlabeled J591 was also examined as an additional control, the mean PSA values 30 days after treatment were 31 ng/ml±20 ng/ml (n=5, untreated animals), 36 ng/ml±38 ng/ml (n=5, 0.02 mg J591-treated animals), 26 ng/ml±21 ng/ml (n=10, Bi-213-HuM195-treated animals), and 12 ng/ml±8 ng/ml (n=12, Bi-213-J591-treated animals) (FIG. 7).

In this experiment, animals received either one single Bi-213 drug administration or four consecutive daily administrations of a smaller dose of drug. There were no statistically significant differences in the responses, i.e., measured PSA levels, observed between the 1× daily and the 4× daily treatment regimens for the Bi-213-J591 and the Bi-213-HuM195 treatments, respectively, nor between the unlabeled J591 and untreated controls. Reduction of PSA levels, however, in all mice (n=12) treated with Bi-213-J591 (1× daily and the 4× daily treatment regimens pooled) relative to all mice (n=10) treated with Bi-213-HuM195 (1× daily and the 4× daily treatment regimens pooled) and all control animals (groups untreated and treated with unlabeled J591 pooled; n=10) was significant with $p<0.0443$ and $p<0.0192$, respectively.

TABLE 3

P for the observed PSA values between the Bi-213-J591-treated mice and the Bi-213-HuM195-treated mice and controls

|  | Bi-213-HuM195 | Controls |
|---|---|---|
| Day 30 Bi-213-J591 (n = 12) | p < 0.0443 (n = 10) | p < 0.0192 (n = 10) |
| Day 51 Bi-213-J591 (n = 6) | p < 0.007 (n = 6) | p < 0.0136 (n = 4) |

Example 14

Killing Larger Tumors by Alpha Particle Killing of Vasculature

Because the ligand carrying the alpha-emitting isotope is unlikely to diffuse into a large tumor during the period in which the isotope is still radioactive, due to the short half life of the isotopes, an alternative method for killing with these constructs is to kill without the need for diffusion. For example, it is possible to rapidly deliver within a few minutes the alpha-emitting ligand to the blood in the well-vascularized tissues and organs. If one can target the tumor vasculature itself, rather than the tumor cells, it will be possible to kill the tumors selectively by this method. Such a method has been demonstrated for native or chemotherapy conjugated ligand or antibody (32). No suggestion of using an alpha particle emitting construct was envisioned in this prior art. However, based on the data contained here, it can be inferred that such an approach would be successful as well. One such ligand capable of targeting vasculature is the J591 antibody (33). This antibody targets the PSM antigen found selectively on tumor vasculature as well as on prostate cancer cells.

In contrast to the teachings of the prior art, solid tumors can be treated by alpha conjugated ligands and it is possible to kill larger tumors using short-lived alpha-emitting ligands. The present invention demonstrated in an in vitro model using tumor clusters "spheroids" containing many thousands of cells that it is possible to first selectively kill the outer layers of a tumor (2-4 cells thick) and thus expose the next inner layers for killing. In this way, by repeated doses of drug, separated in time to allow the death of the outer layers, it is possible to kill larger tumors. This method can be likened to "skinning an onion" and was not obvious until it was demonstrated in vitro and in vivo herein. Finally, it was shown to be true in a live animal model bearing macroscopic tumors.

Cell killing experiments showed specific cell killing with the (Bi-213)CHX-A-DTPA-HuM195, (Bi-212)CHX-A-DTPA-HuM195 and (Bi-213)CHX-A-DTPA-J591 constructs which was dependent on both dose and specific activity of labeling. Both bismuth isotopes showed approximately 50% killing when two bismuth atoms were initially bound onto the target cell surface. Because there are about 10,000 CD33 sites per cell, this implies that only 1 mAb in several thousand will need to be labeled in order to get high levels of cell kill. Because of the rapidly diminishing solid angle occupied by the target cells relative to the IgG in solution, the possibility that alpha-particles that are emitted from starting points beyond the target cell surface may hit the cell nucleus becomes negligible at short distances away from the cell. Similarly, the most efficient cell killing will occur from those emissions that occur from internalized bismuth. An emission from a surface bound IgG may also pass harmlessly away from the cell. Because approximately 50% of radiolabeled CHX-A-DTPA-HuM195 is internalized into cell in 60 min., these data suggest that it is likely that one alpha emission from one atom within the cell is capable of killing that cell. When the initial number of bismuth atoms bound per cell is 2 to 2.5 and the average internalization time is 60 min., there are approximately 60% of cells in which no bismuth atom is inside, based on the Poisson distribution and the probability that the bismuth atom is internalized. At high specific activities, 50% killing of HL60 cells at 24 hr was observed with the alpha-emitting constructs at IgG concentrations of 3.3-25 ng/ml (20-160 pM). A conversion to actual bismuth-labeled IgG shows that only 5-10 pg/ml (30-60 fM) of the radioimmunoconjugate are required at the 50% effective dose.

An important characteristic of the curves describing the cell kill by alpha emitters is the marked dependence on specific activity of the radioconjugate. This was shown with 3 experiments, using 2 different alpha-emitting isotopes and both a leukemia and a solid tumor. Because killing requires specific delivery of the bismuth to or into the cell, as the number of bismuth atoms per HuM195 falls to levels near 1 bismuth per 10,000 IgG molecules, the ability to kill targets approaches that seen with a non-specific target cell. In this instance, unlabeled HuM195 competes for sites with the bismuth labeled CHX-A-DTPA-HuM195. This effect is quite pronounced in this system because of the small number of target binding sites (about $1-4\times10^4$) on HL60 cells, and LnCaP cells respectively.

Example 15

Demonstration of the Clinical Usefulness of the High Specific Activity Ligand for Treating a Human Cancer in Patients A clinical experiment or protocol describing one possible use of an alpha-emitting targeted construct follows. This experiment describes the use of the HuM195 IgG1 to target Bismuth-213 to leukemia cells and demonstrates that the constructs are stable, will deliver the isotope to the cells in a human, and will kill leukemia cells without apparent toxicity to non target tissues. Such a scheme might be used with another alpha emitter, such as bismuth-212 attached stably to this or another ligand, such as an antibody or fragment, cytokine, or receptor ligand, each of which is capable of specific and high affinity binding to a target cell or tissue. Moreover, such ligands might be used also to selectively kill nonmalignant targets such as lymphoid cells involved in a pathological process such as inflammation or autoimmunity, or normal bone marrow cells to enable a bone marrow transplant or transplant of another organ or tissue, or overgrown normal cells that need to be killed because they are involved in a pathological process such as coronary artery disease or other vascular occlusive diseases.

The objectives of the clinical protocol are to determine the safety and toxicity of 213-Bi-labeled HuM195 in patients with relapsed or refractory myeloid malignancies, to determine the pharmacology and dosimetry of 213-Bi-HuM195 and to study the biological effects of 213-Bi-HuM195, including the ability to elicit human antihuman antibody (HAHA) responses and antileukemic responses.

Acute myelogenous leukemia (AML) is the predominant type of acute leukemia in adults. While most patients are able to achieve a complete remission with chemotherapy consisting of cytosine arabinoside and an anthracycline, prolonged disease-free survival is less than 20%. Reinduction attempts will produce second remissions in only 20-25% of patients, frequently lasting less than 6 months. Less than 5% of relapsed patients will survive one year.

Chronic myeloid leukemia (CML) is a biphasic disorder of early hematopoietic progenitors. The chronic phase (with a median duration of 4 years) is associated with marked elevations of mature and maturing leukocytes and leads invariably to a blastic phase resembling acute leukemia. Treatment with "a-interferon has been shown to eradicate evidence of the Philadelphia chromosome by cytogenetic analysis in a minority of patients. Treatment with conventional chemotherapy, however, has had no impact on the natural history of this disease. Allogeneic bone marrow transplantation is the only potentially curative option for these patients. Since patients in accelerated or blastic phases of CML generally do not benefit from transplantation, efforts have been made to transplant these patients during the early chronic phase of their disease.

Classified as a myelodysplastic syndrome, chronic myelomonocytic leukemia (CMMOL) is defined by the presence of a monocyte count of greater than 1 H 109/L, monocytosis of the bone marrow, anemia, and thrombocytopenia. Survival ranges from several weeks to years, with a median survival of 30 to 41 months. Treatment is mostly palliative; hydroxyurea can be used to control high peripheral blood leukocyte counts.

The CD33 antigen is distinctive among hematopoietic antigens in its restricted distribution, and M195 (anti-CD33) is effective in targeting leukemia cells in vitro. M195 is a monoclonal IgG2a antibody derived from a mouse immunized with live human leukemic myeloblasts. Binding specificity of M195 is restricted to myeloid and monocytic leukemia cell lines and a fraction of mature adherent monocytes. Approximately 10,000 antibody-binding sites per cell are expressed on myeloid or monocytic leukemia cell lines and 5,000 sites on mature monocytes.

M195 shows targeting to leukemia cells in humans. Ten patients with myeloid leukemias were treated in a phase I trial with escalating doses of mouse M195. M195 was trace-labeled with $^{131}$I to allow detailed pharmacokinetic and dosimetric studies by serial sampling of blood and bone marrow and whole body gamma-camera imaging. Total doses up to 76 mg (40 mg/m$^2$) were administered safely without any immediate adverse effects. Adsorption of M195 onto leukemic cells in vivo was demonstrated by biopsy, pharmacology, flow cytometry, and imaging. Saturation of available binding sites occurred at doses of greater than 5 mg/m2. The entire bone marrow was imaged specifically and clearly beginning within several hours after injection. M195 was rapidly internalized after binding to target cells. An estimated dose of up to 34 rad/mCi was delivered to the marrow, indicating that whole bone marrow ablative doses of $^{131}$I could be carried by M195.

Humanized M195 (HuM195) is a fully humanized M195 construct that has improved biochemical and immunological activities. Complementarity-determining region (CDR)-grafted humanized M195, retaining only the CDRs and other sterically important amino acids from mouse M195 were constructed using human IgG1 frameworks. Sp2/0 mouse myeloma cell lines secreting humanized M195 were grown in vitro and the antibodies were purified on PA-Sepharose by affinity chromatography using sequential pH step elutions. Purity was determined on SDS-polyacrylamide gels stained with Coomassie brilliant blue. The HuM195 construct maintained binding specificity confirmed against a panel of CD33+ and CD33− cell lines by radioimmunoassays.

HuM195 shows specific targeting of leukemia without immunogenicity in vivo. Toxicity, pharmacology, dosimetry, development of human antihuman antibody (HAHA) responses, and antileukemic effects of HuM195 were studied in patients with relapsed or refractory myeloid leukemias. Thirteen patients were treated on a twice weekly schedule for 3 weeks at 4 dose levels ranging from 0.5 to 10 mg/m2. Alpha emitters have now been conjugated via a bifunctional chelate (CHX-A-DTPA) to HuM195 with high efficiency (>90%) and high specific activities (up to 20 mCi/mg)

Example 16

Antibody Production and Labeling

HuM195 is produced by Protein Design Labs, Inc. (Mountain View, Calif.). Sp2/0 hybridoma cell lines secreting HuM195 are grown in serum-free medium. HuM195 is purified from concentrated supernatants by affinity chromatography followed by additional purification steps. HuM195-CHX-A-DTPA is prepared on contract by TSI Washington (Rockville, Md.). HuM195-CHX-A-DTPA is supplied as a solution at 10.6 mg/ml and stored at −70° C.

Clinical grade 213-Bi generators capable of producing 25-50 mCi are prepared at Sloan-Kettering. Actinium is supplied dried onto a glass ampule from the Transuranium Elements Institute in Karlsruhe, Germany. 213-Bi is eluted from the generator and chelated to HuM195-CHX-A-DTPA, followed by separation of Bi-213-HuM195 by size exclusion chromatography. Sensors for OD280 and gamma emissions are used to determine yield and specific activity. Unlabeled HuM195 may be added to adjust the dose as necessary. This will be performed at Sloan-Kettering Institute immediately prior to injection into patients. Bi-213-HuM195 is diluted in normal saline with 1% human serum albumin (HSA) to a total volume of 10 ml for injection. Bi-213-HuM195-CHX-A-DTPA is manufactured and tested according to an FDA approved IND.

The patient eligibility requirements are that (1) patients must have pathologically confirmed diagnosis of AML that is in relapse or refractory to at least 2 courses of standard induction chemotherapy), accelerated or myeloblastic phase of CML, or CMMOL; (2) greater than 25% of bone marrow blasts must be CD33 positive; (3) patients must have a life expectancy of at least 6 weeks and a Karnofsky performance status of >60%; (4) patients must not have received chemotherapy or radiotherapy for at least 3 weeks prior to treatment, except for hydroxyurea which must be discontinued 2 days prior to treatment. Patients must have recovered from the effects of previous treatment and show clear signs of active leukemia. Patients must not have rapidly accelerating blast counts or clinically unstable disease; (5) Patients must have a serum creatinine <1.5 times the upper limit of normal, bilirubin #1.0 mg/dl, and alkaline phosphatase and SGOT #2.5 times the upper limit of normal which represent grade 0 or 1 toxicities by the NCI common toxicity criteria; and (6) Patients must sign informed consent.

Patients are treated on either an outpatient or inpatient basis. Given the short-half life of Bi-213, radiation exposure to hospital staff is minimal and radiation isolation for patients is not required. Patients are monitored by a Radiation Safety Officer and instructed in the proper disposal of waste. Additionally, patients are discharged for two to three hours after infusion, by which time any remaining gamma radiation will be trivial. Patients will receive Bi-213-HuM195 by IV push, in divided doses, 1-4 times daily, 3-4 hours apart. The following dose escalation scheme is employed: Dose Level 1 (0.28 mCi/kg); Dose Level 2 (0.42 mCi/kg); Dose Level 3 (0.56 mCi/kg); Dose Level 4 (0.7 mCi/kg) and so on with further escalations as needed.

Vital signs, e.g., pulse, blood pressure, respiratory rate, temperature, will be monitored and recorded before treatment, 30 and 60 minutes following infusion, and hourly thereafter for 4 hours. The following tests will be done: CBC, differential, platelet count: Twice daily during treatment, then weekly Q 4, then monthly Q 3. Electrolytes, BUN, Creatinine, Biochemistry profile: Daily during treatment, then weekly Q 4, then monthly Q 3. Human antihuman antibodies: Before treatment and monthly thereafter Q 4. Gamma camera imaging: Continuously for 60 min. after injection of the first and last dose and again at 90 min. after injection of first and last dose. Bone marrow and biopsy, including immunophenotyping: 7-10 days and 4 weeks after treatment. Pharmacokinetics: 5, 10, 15, 30, 45, 60, 90, 120, and 180 minutes after first and last dose.

Twelve patients have entered on four dose levels. More than 50 doses of the drug were synthesized according to the specifications and injected into the patients. Doses could be prepared from the generator at least every 3-4 hours. The generator provided drug that met specifications for at least nine days allowing the treatment of patients. Real time pharmacokinetics were assessed by gamma imaging and serial blood work. The drug targeted first to the sites of leukemia and monocyte/macrophage cells in the liver and spleen. The bone marrow was targeted next. Over time, with succeeding injections, uptake into the liver decreased by 50% as sites were saturated, and uptake in the bone marrow increased by 100%, as more drug became available.

The estimated radiation doses in REM to the whole body, kidneys or other non-target organs were 0.03; to the blood, 125; to the liver 600; to the spleen 1400; 1 and to the red marrow, 1100. Target to non-target dose ratios were therefore 25,000-50,000 to one. There was no acute toxicity in any patient. There was no extramedullary toxicity seen in any patient. In most patients, peripheral blood cell counts of leukemia blasts and white cells began to fall within 48 hours after treatment and were reduced by up to 90%. Counts returned within two weeks. The bone marrow at one week showed reduced cellularity and reduced leukemia blast percentages in the majority of patients (up to 70% reduced).

Example 17

Ac-225 Labeled Constructs

Ac-225 labeled constructs are evaluated for stability in vitro at 37° C. using a Protein A Bead assay that evaluates free Ac-225 and Ig-bound Ac-225 (Nikula et al., 1999). Radionuclide detection is carried-out using gas ionization detection (GID) or pulse height multi-channel analysis (MCA) with a high purity Ge detector (HPGe).

The potency and specificity of the relevant Ac-225 labeled constructs vs. labeled control constructs in killing single cells and multicellular spheroids are evaluated in vitro as a function of specific activity and activity concentration. A $^3$H-thymidine incorporation assay is used to ascertain the number of cells surviving exposure to targeted Ac-225. The ability, and where applicable, the rate of internalization, of Ac-225 labeled IgG constructs into target cell lines is investigated as above described for the B1-213 labeled HuM195 construct.

The retention of Ac-225 in individual cells and multicellular spheroids as a function of time is evaluated by exposing an excess of Ac-225 labeled IgG construct to cell antigens, incubating for an appropriate time, washing, and resuspending in fresh media. The reactivity remaining with the cells and the activity in the supernatant and wash is then quantified. The exposed cells and spheroids are held for 10 days which is one Ac-225 half-life and each day the cells are centrifuged and a fixed volume of supernatant and a fixed volume of concentrated cells sampled for the relative levels of Ac-225 and the radionuclide composition of the respective components. Radionuclide quantitation and characterization is carried-out as previously described.

A variety of novel chelating agents that may be potentially more stable in vivo than [Ac-225]CHX-A-DTPA moiety will be utilized. Initially, the chelation capability is investigated to determine the relative kinetics and thermodynamics of actinium chelation. The rate of chelate incorporation of Ac-225 is assessed by instant thin layer chromatography techniques using silica gel impregnated paper and a basic pH, aqueous mobile phase. Thermodynamic stability is assessed on a relative basis vs. EDTA challenge and incubation in serum or media at 37° C. for several days. Chelating agents are evaluated in this fashion to find those capable of rapid on-reaction, high kd, and suitable stability for in vivo utilization. Candidate chelating agents are further developed by preparing constructs with the mAb's studied.

Example 18

Preliminary Results on Ac-225 Constructs

Several Ac-225 labeling conditions have been evaluated and conditions for rapid labeling have been determined. Yields of [Ac-225]-CHX-AHuM195 are 30-40% after 10 minutes at room temperature. Stability of CHX-A-DTPA chelating moiety in vitro was examined at 1, 3, 24 and 96 hours, and the percentage of Ac-225 bound to HuM195 was 100±0, 100±0, 84±2, and 44±13, respectively for duplicate measurements.

HL60 vs. Raji cell killing with [Ac-225]HuM195 at specific activities of 0.12 and 0.0012 Ci/g demonstrated specific, potent cell killing in a 48 hours exposure assay. The LD95 was approximately 0.5, 50, 50, 50 nCi/ml for the HL60 treated with 0.12 Ci/g, HL60 (0.0012 Ci/g), Raji (0.12 Ci/g), Raji (0.0012 Ci/g), respectively. In comparison, the [Bi-213] HuM195 construct at specific activities of 8 Ci/g had LD95 values of approximately 3 and 10 µCi/ml for HL60 and Raji, respectively. This represents a 67-fold decrease in the Ac-225 specific activity vs. Bi-213 and 6000-fold decrease in the amount of activity necessary to kill 95% of the cells.

AL67 and LNCaP.FGC spheroid cell killing experiments at 0.02 to 8 mCi/ml have been carried out and specific spheroid cell kill demonstrated using the HuM195 and J591 antibody constructs, respectively.

Example 19

LNCaP Tumor Model in Mice

A human prostate cancer tumor model was established in male athymic nude mice by intramuscular xenograft of 5E6 LNCaP tumor cells in the hind leg on day 0. Tumor growth in vivo was assessed at several early time points by sacrificing mice and examining the morphology, size, vascularization, and encapsulation of the tumor cells in the leg histologically. Serum PSA levels in xenografted mice were determined on day 10-12 post-xenograft. Mice were treated by intraperitoneal injection of 200-300 nCi Ac-225 labeled anti-PSMA IgG (J591) on day 12-15 post-xenograft. Animals were monitored for survival and PSA following treatment. Controls consisted of irrelevant Ac-225 labeled IgG (B4), doses of unlabeled anti-PSMA IgG, and untreated growth controls were also performed.

Example 20

Ac-225 Therapy Against Solid Tumors

Figure 8:
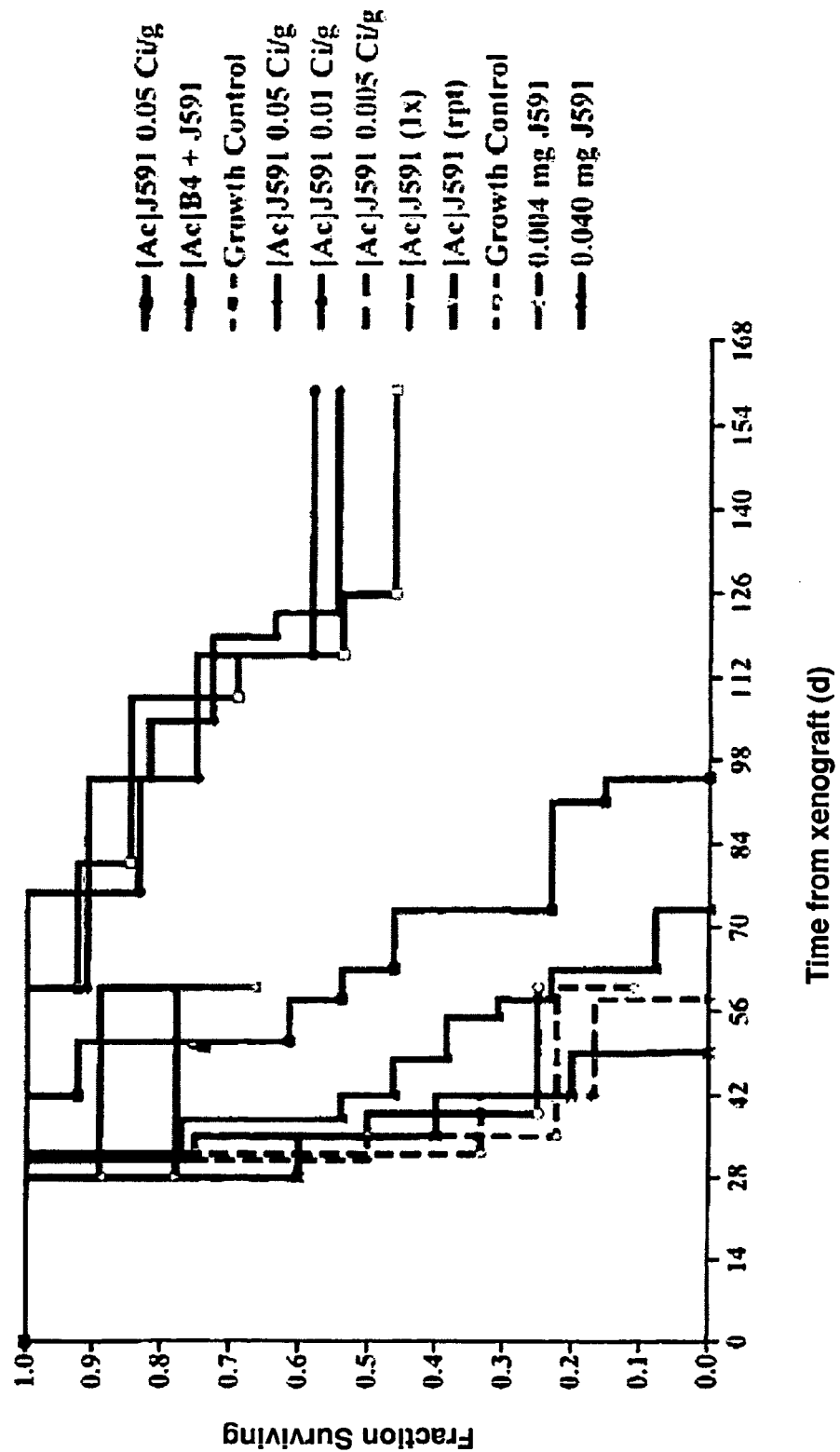
FIG. 8 shows Kaplan-Meier survival plot of fraction of mice surviving tumor-free vs. time for LNCaP xenografted mice treated with Ac-225 labeled anti-PSMA IgG (J591), irrelevant Ac-225 labeled IgG, unlabeled PSMA IgG, and untreated growth controls.

Histopathological evaluation of the LNCaP xenografted mice indicated that tumors were vascularized at day 10, and the encapsulated nodules were found 1 mm×2 mm in size. Serum PSA levels were ranged from 2-5 ng/ml on day 10-12 post-xenograft. FIG. 8 demonstrates composite of Ac-225 RIT I, II, III experiments on LNCaP xenografted mice. It shows that alpha-emitting isotopes attached to monoclonal antibodies targeting the tumors were capable of significantly prolonging the lives of or increasing the curing effect on animals with solid tumors. It is also shown that isotope on irrelevant antibody (B4) were not effective, nor were non-radioactive antibodies.

The following references were cited herein.
1. O'Donoghue et al., (1995) J, Nucl. Med., 36:1902-1909.
2. Willins et al., (1994) J. Nucl. Med., 35:123 P (abstract).
3. Willins et al., (1995) J. Nucl. Med., 36:100-103.
4. Sgouros, G. (1995) J. Nucl. Med., 36:1910-1912.
5. Gerlowski et al., (1986) Microvasc. Res., 31:288-305.
6. Dvorak et al., (1988) Am. J. Path., 133:95-109
7. Jain et al., (1988) Cancer Res., 48:7022-7032.
8. Clauss et al., (1990) Cancer Res., 50:3487-3492.
9. Fujimori, et al., (1990) J. Nucl. Med., 31:1191-1198.
10. Sgouros, et al., (1989) J. Nucl. Med., 30:777 (abstract).
11. Sgouros, G. (1992) J. Nucl. Med., 33:2167-2179.
12. Saga, et al., (1995) Proc. Natl. Acad. Sci., U.S.A., 92, 8999-9003.
13. Riethmuller et al., (1994) Lancet, 343, 1177-1183.
14. Langmuir et al., (1990) J. Nucl. Med. 31:1527-1533.
15. Geerlings et al., (1993) Nucl. Med. Comm. 14:121-125.
16. Simonson et al., (1990) Cancer Res. 50:985s-988s.
17. Huneke et al., (1992) Cancer Res. 52:5818-5820.
18. Macklis et al., (1992) Radiat. Res. 130: 220-226.
19. Kozak et al., (1986) Proc. Natl. Acad. Sci. USA 83:474-478.
20. Scheinberg et al., (1982) Science, 215:1511-1513.
21. Steel, G. G. (1989) Cell Proliferation Kinetics In Tumours. In: Steel, et al., (eds.), The Biological Basis of Radiotherapy, 2nd Ed., Elsevier, Amsterdam.
22. Scheinberg et al., (1989) Leukemia 3:440-445.
23. Caron et al., (1992) Cancer Res. 52:6761-6767.
24. Caron et al., (1994) Blood 83:1760-1768.
25. Schwartz et al., (1993) J. Clin. Oncol. 11:294-303.
26. Co et al., (1992) J. Immunol. 148:1149-1154.
27. Nikula et al., (1995a) Nucl. Med. Biol. 22:387-390.
28. Mirzadeh et al., (1990) Bioconjug. Chem. 1:59-65.
29. Kaspersen et al., (1995) Nucl. Med. Communications 16:468-476.
30. Nikula et al., (1995b) Molec. Immun. 32:865-872.
31. Zamora et al., (1994) BioTechniques, 16:306-311.
32. Arap et al., (1998) Science, 279:377-380.
33. Lui et al, (1997) Ca. Research, 97:3629-3634.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treating a micrometastatic cancer in a patient, the method comprising:
    administering, intravenously, to the patient a conjugate comprising bismuth-213 and an antibody specific for a cancer cell antigen, said micrometastatic cancer comprising a solid micrometastatic tumor with a diameter greater than 1 mm.

2. The method of claim 1, wherein the conjugate is administered at a dose from about 0.1 mg/m$^2$ to about 10 mg/m$^2$.

3. The method of claim 1, wherein the specific activity of the bismuth-213 conjugate is about 20 mCi/mg to about 30 mCi/mg.

4. The method of claim 1, wherein the micrometastatic cancer is in a bone marrow of the patient, is a peritoneal metastasis, or is a cancerous meningitis.

5. The method of claim 4, wherein the cancerous meningitis is in cerebrospinal fluid of the patient.

6. The method of claim 1, wherein the antigen is a tumor vasculature antigen, PMSA, CD3, GD3, CD20, or CD19.

7. A method for treating a micrometastatic cancer in a patient, the method comprising:
    administering intravenously to the patient a conjugate comprising actinium-225 and an antibody specific for a cancer cell antigen, said micrometastatic cancer comprising a solid micrometastatic tumor with a diameter greater than 1 mm.

8. The method of claim 7, wherein the actinium-225 conjugate is administered at a dose from about 0.1 mg/m$^2$ to about 10 mg/m$^2$.

9. The method of claim 7, wherein the specific activity of the actinium-225 conjugate is about 0.1 mCi/mg to about 0.15 mCi/mg.

10. The method of claim 7, wherein the micrometastatic cancer is in a bone marrow of the patient, is a peritoneal metastasis, or is a cancerous meningitis.

11. The method of claim 10, wherein the cancerous meningitis is in a cerebrospinal fluid of the patient.

12. The method of claim 7, wherein the antigen is a tumor vasculature antigen, PMSA, CD3, GD3, CD20, or CD19.

* * * * *